United States Patent
Zhang et al.

(10) Patent No.: US 11,001,746 B2
(45) Date of Patent: May 11, 2021

(54) COMPOSITIONS COMPRISING AND METHODS OF MAKING BIO-POLYMERS

(71) Applicant: GEO FOSSIL FUELS, LLC, Houston, TX (US)

(72) Inventors: Zhaoduo Zhang, Pleasanton, CA (US); William J. Kohr, Gig Harbor, WA (US)

(73) Assignee: GEO FOSSIL FUELS, LLC, Houston, TX (US)

(*) Notice: Subject to any disclaimer, the term of this patent is extended or adjusted under 35 U.S.C. 154(b) by 272 days.

(21) Appl. No.: 16/324,032

(22) PCT Filed: Aug. 2, 2017

(86) PCT No.: PCT/US2017/045078
§ 371 (c)(1),
(2) Date: Feb. 7, 2019

(87) PCT Pub. No.: WO2018/031333
PCT Pub. Date: Feb. 15, 2018

(65) Prior Publication Data
US 2019/0169486 A1    Jun. 6, 2019

Related U.S. Application Data

(60) Provisional application No. 62/372,992, filed on Aug. 10, 2016.

(51) Int. Cl.
*C09K 8/588*   (2006.01)
*C12P 19/04*   (2006.01)
*C12P 19/06*   (2006.01)

(52) U.S. Cl.
CPC ............. *C09K 8/588* (2013.01); *C12P 19/04* (2013.01); *C12P 19/06* (2013.01)

(58) Field of Classification Search
None
See application file for complete search history.

(56) References Cited

U.S. PATENT DOCUMENTS

| | | |
|---|---|---|
| 2,660,550 A | 11/1953 | Updegraff et al. |
| 2,907,389 A | 10/1959 | Hitzman |
| 2,975,835 A | 3/1961 | Bond |
| 3,020,207 A * | 2/1962 | Patton .................. C12P 19/06 435/104 |
| 3,032,472 A | 5/1962 | Hitzman |
| 3,332,487 A | 7/1967 | Jones |
| 4,006,058 A | 2/1977 | Savins |
| 4,353,805 A * | 10/1982 | Kragen .................. C08L 5/00 166/246 |
| 4,412,925 A * | 11/1983 | Ballerini ............... C09K 8/905 507/213 |
| 4,475,950 A | 10/1984 | Finlayson |
| 4,558,739 A | 12/1985 | McInerney et al. |
| 4,799,545 A | 1/1989 | Silver et al. |
| 4,800,959 A | 1/1989 | Costererton et al. |
| 4,905,761 A | 3/1990 | Bryant |
| 4,950,747 A * | 8/1990 | Farrar ..................... C08J 3/09 536/114 |
| 4,971,151 A | 11/1990 | Sheehy |
| 5,163,510 A | 11/1992 | Sunde |
| 5,297,625 A | 3/1994 | Premuzic et al. |
| 6,543,535 B2 | 4/2003 | Converse et al. |
| 6,546,962 B1 | 4/2003 | Sunde |
| 7,472,747 B1 | 1/2009 | Brigmon et al. |
| 8,316,933 B2 | 11/2012 | Kohr |
| 8,357,526 B2 | 1/2013 | Keeler et al. |
| 9,869,166 B2 | 1/2018 | Kohr et al. |
| 10,047,168 B2 | 8/2018 | Mazoyer et al. |
| 10,227,853 B2 | 3/2019 | Kohr et al. |
| 2001/0045279 A1 | 11/2001 | Converse et al. |
| 2009/0020289 A1 | 1/2009 | Sharif |
| 2009/0029879 A1 | 1/2009 | Soni et al. |
| 2011/0067856 A1 | 3/2011 | Kohr |
| 2011/0268846 A1 | 11/2011 | Nair et al. |
| 2012/0261117 A1 | 10/2012 | Pavia et al. |
| 2012/0273189 A1 | 11/2012 | Alsop et al. |
| 2013/0062053 A1 | 3/2013 | Kohr et al. |
| 2014/0315765 A1 | 10/2014 | McDaniel |
| 2017/0064966 A1 | 3/2017 | Opatowsky et al. |

FOREIGN PATENT DOCUMENTS

| | | |
|---|---|---|
| BR | 1020120282380 | 12/2014 |
| WO | 199213172 | 8/1992 |
| WO | 2012116230 | 8/2012 |
| WO | 2015038820 | 3/2015 |

OTHER PUBLICATIONS

Cao et al., "Engineering behavior and characteristics of water-soluble polymers: implication on soil remediation and enhanced oil recovery," (2016) Sustainability 8:1-16.
Da Silva et al., "Lytic enzyme production optimization using low-cost substrates and its application in the clarification of xanthan gum culture broth," (2014) Food Science & Nutrition 2(4):299-307.
Safdel et al., "Microbial enhanced oil recovery, a critical review on worldwide implemented field trials in different countries," (2017) 74(21):159-172.
Branda et al., "A major protein component of the Bacillus subtilis biofilm matrix," (2006) Mol. Microbiol. 59(4):1229-1238.
Chu et al., "Targets of the master regulator of biofilm formation in Bacillus subtilis," (2006) Mol. Microbiol. 59(4):1216-1228.
Colvin et al., "The Pel and Psl polysaccharides provide Pseudomonas aeruginosa structural redundancy within the biofilm matrix," (2012) Environ. Microbiol. 14(8).
Darzins et al., "Clustering of mutations affecting alginic acid biosynthesis in mucoid Pseudomonas aeruginosa," (1985) J. Bacteriol., 164(2):516-524.
Dogsa et al., "Exopolymer diversity and the role of levan in Bacillus subtilis biofilms," (2013) PLoS One 2013 8(4):e62044.

(Continued)

*Primary Examiner* — John J Figueroa
(74) *Attorney, Agent, or Firm* — Venable LLP; Keith G. Haddaway

(57) ABSTRACT

A method is provided for the production of an aqueous composition suitable for direct use in a water-flood oil recovery process, which comprises a clarified fermentation fluid containing at least one dissolved polysaccharide, along with the clarified fermentation fluid and aqueous compositions prepared by such method.

21 Claims, No Drawings

(56) References Cited

OTHER PUBLICATIONS

Ghafoor et al., "Role of exopolysaccharides in Pseudomonas aeruginosa biofilm formation and architecture," (2011) Appl. Envir. Microbio. 77(15):5238-46.
Hay et al., "Impact of alginate overproduction on attachment and biofilm architecture of a supermucoid Pseudomonas aeruginosa strain," (2009) Appl. Environ. Microbiol. 75(18):6022-25.
Karatan et al., "Signals, Regulatory Networks, and Materials that Build and Break Bacterial Biofilms," (2009) Microbiol Mol Biol Rev 73(2):310-47.
Katzen et al., "Promoter analysis of the Xanthomonas campestris pv. campestris gum operon directing biosynthesis of the xanthan polysaccharide," (1996) J. Bacteriol. 178(14):4313-18.
Kim et al., "Application of LFH-PCR for the disruption of SpoIIIE and SpoIIIG of B. subtilis," (2000) Biotechnol. Bioprocess Eng. 5(5):327-31.
Ma, "The Roles of Biofilm Matrix Polysaccharide Psl in Mucoid Pseudomonas Aeruginosa Biofilms," (2012) FEMS Imuunol Med Microbiol 65:377-380.
Makarova et al., "Comparative genomics of Archaea: how much have we learned in six years, and what's next?" (2003) Genome Biology, 4(8) article 115.
Mann et al., "Pseudomonas Biofilm Matrix Composition and Niche Biology," (2012) FEMS Microbiol Rev 36(4):893-916.
Mathee et al., "Mucoid conversion of Pseudomonas aeruginosa by hydrogen peroxide: a mechanism for virulence activation in the cystic fibrosis lung," (1999) Microbiology 145:1349-57.
O'Toole et al., "Initiation of biofilm formation in Pseudomonas fluorescens WCS365 proceeds via multiple, convergent signalling pathways: a genetic analysis," (1998) Mol. Microbiol. 28(3):449-61.
Pollock et al., "Production of xanthan gum by Sphingomonas bacteria carrying genes from Xanthomonas campestris," (1997) J. Ind. Microbiol. Biotech. 19:92-7.
Robleto et al., "Genetic analysis of the AdnA regulon in Pseudomonas fluorescens: nonessential role of flagella in adhesion to sand and biofilm formation," (2003) J. Bacteriology 185(2):453-60.
Romero et al., "Amyloid fibers provide structural integrity to Bacillus subtilis biofilms," (2010) PNAS 107(5):2230-34.
Suppiger et al., "The DSF Type Quorum Sensing Signalling Systems RpfF/R Regulates Diverse Phenotypes in the Opportunistic Pathogen Cronobacter," (2016) Nature, Scientific Reports, p. 1-8.
Vlamakis et al., "Sticking Together: Building a Biofilm the Bacillus Subtilis Way," (2013) Nature Review Microbiology 11:157-68.

* cited by examiner

COMPOSITIONS COMPRISING AND METHODS OF MAKING BIO-POLYMERS

BACKGROUND OF THE INVENTION

Bio-polymers are hydrophilic polysaccharides, which may be obtained by the fermentation in appropriate nutrient media using microorganisms of the genera *Xanthomonas, Sphingomonas, Pseudomonas, Klebsiella, Erwinia, Alcaligenes, Asotobacter, Clostridium, Sclerotium, Schizophyllium, Corticium, Stromatinia*, and the like. When dissolved in water in low concentration, the high molecular weight soluble polysaccharides increase the viscosity of the aqueous solution. The resulting viscosified solutions are used in a wide variety of industrial applications, such as food additives and industrial thickeners and cosmetics. During commercial preparation polysaccharides the polysaccharides unattached to the cell wall are usually recovered by alcohol precipitation from the fermentation broth in which they are made. The viscosity of the broth is generally very high by the end of the fermentation. Therefore, it is generally considered not feasible to separate all extraneous fermentation solids and dissolved media components before the first precipitation step. For example, U.S. Pat. No. 4,326,052 (Kang et al.) describes a process where the soluble polymers are first precipitated by 2 parts isopropanol to one part fermentation broth. The precipitate is removed by centrifugation and then dried. The dried material contains not only polysaccharide, but also generally contains proteins, bacterial cells, cell debris and other insoluble material. The first precipitate generally dried and is then dissolved in water and centrifuged again to remove the insoluble solids, such as nonviable bacterial cells and other cellular debris. These solids are difficult to dissolve when the polysaccharide polymer is redissolved in water and the resultant solution is generally not clear. Further clarification of this dissolved bio-polymer is difficult because the cells and cell debris are only slightly denser than the viscous solution itself. Removal of cell aggregates and proteins may require lengthy centrifugation at high speed. While the presence of these solids is not objectionable in many cases, it is problematic in the applications where the bio-polymer is used to increase the viscosity of a water flood solution that is injected into oil containing underground formations as a process of enhanced oil recovery (EOR).

In the special application of EOR, the polymer solution must be extensively clarified. In this case of EOR by the polymer flooding of oil containing formations, the residual cells, cell debris and cell aggregates can clog the sandstone formation. This can cause an increase in the resistance to flow and require higher pressure to maintain flow. An increase in pressure can fracture the formation and cause other costly problems. This is called a loss of injectivity or a loss of filterability. Loss of injectivity can be a problem with any polymer both bio-polymer and chemical polymer that are used for EOR. Generally debris in the dissolved polymer solution is the number one reason for loss of injectivity as described in Seright, R. S., Seheult, J. M., & Talashek, T. (2008 Jan. 1), Injectivity Characteristics of EOR Polymers. Society of Petroleum Engineers. doi: 10.2118/115142-MS.

In high salinity displacement fluids a polysaccharide viscosifying agent such as those derived from *Xanthomonas campestris* and other polysaccharide producing microorganisms are desirable. However, these bio-polymer can have a major problem that has not been completely solved. This problem concerns the presence of insoluble cell debris in industrial grades of these polysaccharide solutions. In the typical commercial production of polysaccharides by e.g. *Xanthomonas* fermentation, the high viscosity of the fermentation broth complicates the complete separation of insoluble material, such as cellular debris and nonviable bacteria from the polysaccharide-containing broth.

Methods described go address this problem by dissolving the insoluble proteins have included enzyme treatments. For example, U.S. Pat. No. 4,010,071 discloses a method of clarifying xanthan solutions by treating with an alkaline protease. EP 0078621 and GB 2111520 disclose a process for clarifying xanthan gum solutions by treatment of the solution with an acid or neutral protease, followed by increasing the pH of the solution from pH 8 to 13. Another group of enzymes that are suggested is polysaccharase as described by N. Kohler et al. Clim. Past 11: 1801-183, 2015 (SPE-10712). U.S. Pat. No. 5,595,892 discloses a method for recovering and purifying xanthan gum from a fermentation broth by heating the broth to a temperature of 45 degrees Celsius to 80 degrees Celsius at a pH of 7.0 to 12.5, and then treating the solution stepwise with an alkaline protease and a lysozyme. EP 0549230 and U.S. Pat. Nos. 5,679,556, 5,702,927, 5,705,368 and 5,994,107 disclose related methods wherein a fermentation broth is heated at a temperature of 45 degrees Celsius to 70 degrees Celsius at a pH of at least 9.0, followed by enzyme treatment, wherein the order of alkaline protease and a lysozyme enzyme treatments is interchangeable.

Another treatment with protease enzymes has been described in U.S. Pat. No. 4,119,491. To improve the clarification an enzymatic digestion is initiated. However before the cell bodies are completely disintegrated the solution is contacted with particles of solid siliceous material at an adsorption-enhancing pH followed by filtering-out the siliceous solids and the partially-disintegrated cell bodies that are adsorbed on them.

In U.S. Pat. No. 4,416,990 a process is described for enzymatically purifying of a polysaccharide containing as impurities bacterial cell residues and microgels. This process comprises the treating of an aqueous solution of the bio-polymer with the enzyme Basidiomycete cellulase.

In U.S. Pat. No. 4,326,037 a method is described for enhancing the ability of polysaccharides in aqueous solutions to flow through a porous medium which comprises contacting the polysaccharides with an endoenzyme which is capable of hydrolyzing at least one of the linkages of the sugar units of the polysaccharides. This process requires maintaining the polysaccharides in contact with the enzyme under hydrolysis conditions for a time sufficient to decrease the tendency of the polysaccharides to plug the porous medium yet insufficient to decrease the viscosity of the aqueous polysaccharides by more than 25%. Unlike proteases which only digest proteins, these enzymes describe in U.S. Pat. No. 4,326,037 can digest the polysaccharides and reduce the overall viscosity left go too long.

Efforts are still being made to improve the filterability of a polysaccharide containing aqueous solutions. The term filterability is commonly used to describe the ability of a fluid to flow through a porous medium, and derives from the filtration test employed in the oil industry. U.S. Pat. No. 4,431,734 describes an enzymatic process for the treatment of polysaccharide gums for improving the filterability of their aqueous solutions. In this process a combination of two enzymes i.e. a polysaccharase and protease is used.

Another method previously disclosed in U.S. Pat. No. 4,729,958 claiming use of DNAase to increase filterability by dissolving the polymers of DNA. These DNA digesting enzymes are believed to dissolve the DNA polymers which might be part of the cell debris and cell aggregates.

Other approaches known in the art use a siliceous material to remove cell debris. A method of improving the removal of the partly degraded cells is described in U.S. Pat. No. 4,119,491. The siliceous materials, for providing surfaces on which the partially disintegrated bacterial cell bodies (which have been separated from the associated polymers by the enzyme treatment) can be adsorbed can comprise any such particulate and/or fibrous siliceous materials such as sand, glass wool, diatomaceous earth, or the like materials. Particularly suitable materials are relatively coarse diatomaceous earth, filter-aid materials having particle sizes of from about 1 to 300 microns. It is important that the pH of that solution be in the order from about 10 to 11. Various procedures can be used for contacting the solution with the siliceous material; for example, the solution can be pumped directly through a sand or glass wool filter in which the siliceous material particle sizes and filtration rate are arranged so that the bacterial debris is adsorbed on the solids and the solids are filtered out as the solution moves through the filters. Where particulate siliceous solids, e.g., diatomaceous earth, filter-aid particles are used, such solids can advantageously be added to a stream of the solution upstream of the filter. The filtration of the suspension of siliceous solids and adsorbed bacterial cell bodies from the aqueous polymer and enzyme-containing solutions can be effected by flowing the liquid components through substantially any filter bed means capable of removing the siliceous solids on which the disassociated bacterial bodies are adsorbed. Earlier methods disclosed in U.S. Pat. Nos. 3,711,462 and 3,729,460 removed cell debris with clay and clay at pH 11.8 to 12.8.

Although these methods may provide clarified bio-polymer solutions with some improvement in filterability, they require several processing steps, sometimes under different processing conditions, such as pH or changes in temperature, which may result in increased manufacturing costs due to the complexity of the entire process. Additionally the multi step process requires a large and high capital cost facility for producing a powdered form of polysaccharide bio-polymer that can be shipped to an oil field where needed for polymer enhanced oil recovery. Accordingly, there is a need for a simplified and effective process for the preparation of clarified soluble polysaccharide solutions of high enough viscosity and high enough purity and injectivity to be produced in proximity to an oil field so that it can be economically injected into the formation for enhanced oil recovery.

BRIEF DESCRIPTION OF THE INVENTION

In one aspect, the invention concerns a method for the production of an aqueous composition suitable for direct use in a water-flood oil recovery process, which comprises a clarified fermentation fluid containing at least one dissolved polysaccharide, said method comprising the consecutive steps of:

(a) culturing a polysaccharide-producing microorganism in an aqueous culture medium to produce an aqueous culture containing said dissolved polysaccharide therein; and (b) clarifying the resultant aqueous culture from step (a), the clarification being effected by an addition of at least one soluble metal ion known to form insoluble precipitates with anions of sulfate, phosphate or carbonate in excess of the amount of said anions in the fermentation broth; and (c) incubating the metal ions with the fermentation broth to form a precipitate on the cells and cell debris;

(d) removing the precipitate by gravity settling and/or centrifugation, and recovering said resultant clarified fermentation fluid containing said dissolved polysaccharide;

wherein said steps (a)-(d) follow each other in this order, without any intervening steps.

By this process, the dissolved polysaccharide is obtained without precipitation and recovery of a solid polysaccharide and dissolution thereof in an aqueous medium and is suitable for direct use in water-flood oil recovery processes.

In one embodiment, the method consists essentially of steps (a)-(d).

In another embodiment, the method consists of steps (a)-(d).

In another embodiment, the clarification treatment is effected by centrifugation of at least 4,000 g.

In yet another embodiment, the polysaccharide-producing microorganism is a microorganism of the *Xanthomonas* type.

In a further embodiment, the aqueous composition has a polysaccharide concentration of 0.005 to 1% by weight and a viscosity of from 5 to 500 centipoises at the reservoir temperature.

In a still further embodiment, the precipitating agent is soluble salt of a metal ion known to form low solubility salts of sulfate, carbonate or phosphate.

In one embodiment, the precipitating agent is barium ion.

In another embodiment, the precipitating agent is strontium ion.

In yet another embodiment, the precipitating agent is calcium ion.

In yet another embodiment, the precipitating agent is zinc ion.

In a further embodiment, the precipitating agent is lead ion.

In a still further embodiment, the precipitating agent is mercury ion.

In another embodiment, the precipitating agent is magnesium ion.

In a further embodiment, the microorganism is *Xanthomonas campestris*.

In a still further embodiment, 3 the microorganisms are selected from the group consisting of the *Xanthomonas* genus, particularly the *Xanthomonas campestris, Xanthomonas begoniae, Xanthomonas pisi, Xanthomonas vesicatoriae, Xanthomonas carotae, Xanthomonas hederae, Xanthomonas incanae, Xanthomonas malvacearum, Xanthomonas phaseoli, Xanthomonas vasculorum, Xanthomonas vitians* and *Xanthomonas pelargonii* species, of the *Arthrobacter* genus, particularly the *Arthrobacter stabilis* and *Arthrobacter viscosus* species, of the *Erwinia* genus, particularly the *Erwinia Tahitica* species, of the *Azotobacter* genus, particularly the *Azotobacter indicus* species, etc. and fungi of the *Sclerotium* genus, preferably the *Sclerotium glucanicum* and *Sclerotium rolfsii* species.

In another aspect, the invention concerns a clarified fermentation fluid obtained by a method hereinabove described.

In various embodiments, the method comprises, consists essentially or, or consists of steps (a) to (d) of the method hereinabove described.

In yet another aspect, the invention concerns an aqueous composition suitable for direct use in a water-flood oil recovery process, which comprises a clarified fermentation fluid containing at least one dissolved polysaccharide, such clarified fermentation fluid being obtained by a method hereinabove described.

In various embodiments, the method comprises, consists essentially or, or consists of steps (a) to (d) of the method hereinabove described.

DETAILED DESCRIPTION OF THE INVENTION

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The term "bio-polymer", as defined herein, refers to hydrophilic polysaccharides, which are produced by a living cell. In particular, bio-polymers may be obtained by the fermentation in appropriate nutrient media by microorganisms, including microorganisms of the genera *Xanthomonas, Sphingomonas, Pseudomonas, Klebsiella, Erwinia, Alcaligenes, Asotobacter, Clostridium, Sclerotium, Schizophyllium, Corticium, Stromatinia*, and the like. Sugar-based bio-polymers (polysaccharides) can be linear or branched and are typically joined with glycosidic bonds. The exact placement of the linkage can vary, and the orientation of the linking functional groups is also important, resulting in α- and β-glycosidic bonds with numbering definitive of the linking carbons' location in the ring. In addition, many saccharide units can undergo various chemical modifications, such as amination, and in some cases can form parts of other molecules, such as glycoproteins. In a particular embodiment, the bio-polymer is a Xanthan gum polysaccharide secreted by the bacterium *Xanthomonas campestris*. It is composed of pentasaccharide repeat units, comprising glucose, mannose, and glucuronic acid. It is usually produced by the fermentation of glucose, sucrose, or lactose.

The term "oil reservoir" is used herein in the broadest sense and includes all forms of hydrocarbon deposits, including, without limitation, underground reservoirs, producing wells, non-producing wells, experimental wells, exploratory wells, oil sands and other sources of heavy oil and the like, which may be accessible by any means, such as, for example, one or more wellbores.

DETAILED DESCRIPTION

The demand for crude oil has exceeded the existing production in the United States for more than 30 years. This has led to increasing demand for more imported oil and a dependency on foreign suppliers. The growth of emerging economies is rapidly increasing the demand for oil in the global market. It has been estimated that more than half of all conventional oil (oil that can be produced with current technology) has been produced. Most of the remaining conventional oil is located in the Eastern Hemisphere or in environmentally sensitive areas such as the North Pole. The lack of conventional oil supplies could keep oil prices so high that oil dependent nations such as the United States would be unable to fund the development of alternative energy technologies and be forced into dependency on foreign alternative energy as well. Therefore any new technology that could increase the efficiency of oil recovery would be of great benefit to countries such as the U.S. that have large amounts of unrecoverable oil in place (OIP) in older exiting oil fields.

Most oil fields are small and are spread out in the 600 or so sediment basins throughout the world. Most of these oil-producing basins have been explored. Generally the largest fields are discovered first, and further exploration finds only smaller reservoirs. Most of the world's petroleum is found in large fields. Only 37 supergiant oil fields of over 5 billion barrels have been found. These 37 fields account for 80% of all the known oil. Only two of these supergiants are in North America and 26 are in the Persian Gulf. Most of the remaining undeveloped oil in the Western Hemisphere is not light petroleum, but is heavy oil or tar sands. Large deposits of heavy oil are in Venezuela and California. Canada has large deposits of tar sands. Currently, production of heavy oil requires large amounts of energy.

Most petroleum is found in sandstone, siltstone or carbonate. Porosities vary from 5% to 30%. The porous rock, covered with an impermeable layer, collects oil from organic matter in lower source rock. It is a process that takes millions of years. The maturation process converts it to a complex mixture of hydrocarbons of about 82 to 87% carbon and 12 to 15% hydrogen. The oil moves into the porous rock in low concentrations with water. To become a reservoir the porous rock must have some type of impermeable cap-rock that traps the oil. Most traps are anticlinal upfolds of strata that are oval shape, however, fault-traps and salt-domes are also common. Oil near the surface often encounters descending meteoric water that brings in oxygen and bacteria that degrade the oil to heavy oil or tar. Oil is usually not found below 4,900 meters because the high temperature of deep rock will degrade the petroleum into natural gas. Therefore, most oil is between 760 m and 4,900 m deep.

Unlike natural gas, the recovery of petroleum oil is not efficient. The existing conventional oil production technologies are able to recover only about one-half of the oil originally in place in a reservoir of light oil. For heavy oil, the recovery is often less than 10%. Tar sands are so heavy that they will not flow at all and no oil can be recovered by conventional drilling and pumping. A technology that could recover a greater percentage of this residual oil could increase oil production from existing reservoirs and reduce the need of the U.S. for imported oil. The additional oil recovered from existing oil producing reservoirs could reduce the need to explore and develop wilderness areas that are potential new oil fields. This additional recovery of existing oil could bridge the gap needed for the development of alternative renewable energy sources.

The Original Oil In Place (OOIP) is the petroleum present in the oil reservoir when first discovered. The volume of the reservoir is determined by the size and porosity of the carbonate or sand stone. The porosity of the rock is a measure of the amount of small chambers or micro-traps within the rock that can hold water or oil. The oil is generally pushed up to the surface with the existing oil reservoir pressures at first. The pressure in the oil well drops with time and there is a need to create overpressure with other means such as water injection or a gas injection for secondary recovery of the OOIP. The choice of a specific secondary recovery technique depends on the type of the hydrocarbon accumulation and the nature of the reservoir. Water injection or "water sweep" or "waterflooding" is a common secondary recovery technique. In waterflooding, pressurized water is injected into the oil-bearing formation rock. Ideally, the injected water displaces the residual oil and moves it to a producing well. Generally in waterflooding, crude oil free of water is recovered first, and then subsequently a mixture of crude oil and water are recovered from the production wells. At some point, the percentage of water in the oil-water mixture (referred to as the water cut) from this technique becomes so high that it is uneconomical to continue pumping oil from the well. The problem, with using water as a "drive fluid", is that water and oil are immiscible. The lower viscosity water will flow over the oil and by-pass large amounts of oil. Therefore, even after secondary recovery, a significant portion of crude oil remains in the formation, in some cases up to 75% of the OOIP. The fraction of unrecoverable crude oil is typically highest for heavy oils, tar, and large complex hydrocarbons. In the U.S. this residual OIP in old oil wells could be as much as 300 billion barrels of light oil. World-wide, the estimate of unrecoverable oil is 2 trillion barrels. There are an additional 5 trillion barrels of heavy oil, most of which is unrecoverable. Much of this remaining oil is in micro-traps due to capillary forces or adsorbed onto mineral surfaces (irreducible oil saturation) as well as bypassed oil within the rock formation.

Oil recovery can be improved by a variety of thermal and non-thermal methods. Non-thermal methods are best suited for recovery of light and moderately viscous oils. The major objectives for these processes are to lower the interfacial tension (IFT) between the oil and displacing fluid and to improve the mobility ratio. Several non-thermal processes have been experimented with or used over the years. Many of these rely on surfactants for reducing the oil viscosity and decreasing the IFT between the oil and displacing fluid. Ideally, the mobility of the displacing fluid should not be higher than the oil. The mobility ratio (mobility of displacing fluid over mobility of displaced fluid) should be low. The mobility of the oil can be increased by viscosity reduction and by IFT reduction. As the IFT is decreased, the oil becomes more miscible with the fluid until it becomes one phase and the IFT is zero. This decreases the mobility ratio and increases the oil recovery. Alternatively, the viscosity of the displacing fluid can be increased by adding polymers to "thicken" the liquid. Non-thermal methods require less energy and are best suited for light oil of 100 cp or less. However, most non-thermal methods require considerable laboratory experimentation and process optimization. The high cost of surfactants and polymers is generally the limiting factor for chemical EOR.

There are two major classes of chemical or non-biological EOR. One is miscible flooding with a displacing fluid that is miscible with the reservoir oil and will reduce the IFT to zero. The displacing fluid can, for example, be a chemical formulation. The chemical compounds interact with the oil or the water or both in such a way that there is a decrease in mobility ratio and IFT which leads to better oil mobility and recovery. Chemical methods have a major advantage over both thermal and compressed gases in that they generally have lower capital requirements and are not limited by location and availability of gases or sources of inexpensive heat energy. Economics is the major deterrent to the use of chemical EOR. Many of the chemicals used in these processes are manufactured from petroleum and their cost increases as the price of oil increases. Government subsidies are often needed to spur the use of these costly chemical methods in order to increase the production of domestic oil from mature wells.

There are several chemical flooding processes, including polymer flooding, which functions by improving the mobility ratio and reducing the permeability contrast of the reservoir. In most cases a slug of polymer solution of about 20 to 40% of the reservoir pore volume is pumped into the injection wells. Losses of polymer to the porous reservoir rock and degradation of the polymer due to shear forces can limit the success of the method. The polymers can be synthetic chemical polymers such as polyacrylamide or biologically produced such as polysaccharides. Some biopolymers are more effective at high salinity than the chemical polymers, but are also more expensive to produce.

Microbial enhances oil recovery (MEOR) processes use microorganisms to achieve the objective of lowering the interfacial tension (IFT) between the oil and displacing fluid and to improve the mobility ratio of the water drive to fluid oil. The major mechanisms by which microbes are believed to function by are: (1) alteration of the permeability of the subterranean formation by producing low molecular weight acids from the biodegradation of hydrocarbons that cause rock dissolution, (2) production of bio-surfactants that can decrease IFT and form micelles of oil in water in a way similar to chemical surfactants, (3) mediation of changes in wet-ability of the oil droplet by growing on the droplet and changing the surface of the oil to a less hydrophobic surface (4) production of bio-polymers that improve the mobility ratio of water to petroleum by increasing the viscosity of water and plugging high flow channels, (5) production of lower molecular weight hydrocarbons by enzymatically converting the large hydrocarbons into smaller molecules, which will reduce of the oil's viscosity, (6) generation of gases (predominantly carbon dioxide and nitrogen) that increase formation pressure.

These approaches can be combined and supplemented in order to provide optimal result.

The present invention provides improvement in MEOR.

In particular, this invention concerns an improvement to oil recovery from oil formations by injection of viscosifying solutions of bio-polymers prepared by reacting microorganisms with carbohydrates; it particularly relates to the direct injection, without bio-polymer isolation by alcohol precipitation, of the fermentation fluid prepared according to this method, after separation of at least the major portion of the cells and cell debris by co-precipitation with metal sulfides, phosphates and or carbonates. The denser mixture of cells, cell debris and insoluble metal sulfides, phosphates and or carbonates are more readily separated by gravity means such as settling and centrifugation than prior method of cells and cell debris removal by either centrifugation or filtration. Unlike prior methods which attempted to remove cells and cell debris from the high viscosity solutions of bio-polymer by multi-step processes requiring long incubation times with enzymes and surfactants followed by high speed centrifugation and filtration this new method combines removal of residual anions of sulfate, phosphate and carbonate in the fermentation media which can interact with the formation water ions to cause scaling problems in the formation rock. These residual anions are removed from the fermentation broth by the addition of excess amounts of metal cat ions to the broth that can form insoluble precipitates and thereby effectively remove any anion that may cause scaling within the oil formation when the polymer fluid comes in contact with the metal ions in the formation water. It was discovered that the anion precipitation surprisingly also removes cell debris that can cause bio-plugging of the formation rock. The combined mixture of cells, cell debris and insoluble metal sulfides and carbonates and phosphates are significantly denser than the fermentation polymer broth or the cell debris alone and thereby faster to centrifuge out of the suspension.

An aqueous solution of soluble polysaccharides is directly recovered from a whole fermentation broth containing cell free polysaccharides producing microorganism after precipitation of cells, nutrient ions, cell debris and other insoluble material. Polysaccharides polymer that are produced by fermentation of simple sugars by bacteria such as the bacterium *Xanthomonas campestris*, which is described in U.S. Pat. No. 3,659,026 requires complex and expensive purification before they can be used in applications such as polymer flooding EOR. This new disclosed method can produce a soluble viscous solution of bio-polymer for direct injection and or mixing with formation water for injection into an injection well.

Unlike prior methods of recovering bio-polymers from fermentation broth that precipitate the water soluble polymer with two or more volumes of alcohol, this method first precipitates the cells, cell debris, cell aggregates and residual media salts by the addition of a precipitating agent. The precipitating agent comprises a mixture of metal ions in solution that bind with the cells, cell debris and cell aggregates while forming insoluble precipitates with the sulfates, phosphates and carbonates in the fermentation broth. Once formed these precipitates have greater density that the cell, cell debris, and cell aggregates can be removed by high throughput centrifugation. The produced viscous soluble bio-polymer solution can be further purified and clarified by the addition of enzymes to degrade any un-precipitated cell material. Alternatively the soluble polymer solution or the mixture of polymer and recovered production water may be filtered before injection into the well. It is intended that this process is simple enough that it can be used to produce a bio-polymer fluid for polymer flooding EOR at or near the well site, thereby greatly reducing the cost of the bio-polymer.

This method of recovering soluble polysaccharide directly from a fermentation broth is designed to be simpler and faster and of lower overall cost and complexity than prior methods that require alcohol precipitation, drying and clarification with multi-enzyme processes. The process describe herein removes component in the fermentation broth by precipitating these components from the soluble polysaccharide polymer solutions rather than precipitating the soluble polymer from the broth solution.

The treating agent used herein may be comprised of a single agent or a combination of agents, according to the different embodiments described herein. For example, a solution of metal cations may be made from process water or concentrated process water or added soluble cat ion salts known to precipitate residual phosphates and sulfates remaining in the fermentation broth. A surfactant may be used individually or in combination with one or more enzymes to further clarify the polymer broth solution. These agents may be used individually or combined in any manner, together with a protease enzyme or a lysozyme and a polysaccharase enzyme, to provide the high purity xanthan gum of this invention. Preferred treating agent combinations include the soluble ions of barium, calcium, strontium, iron, magnesium, zinc, lead, mercury, silver and other metals that form insoluble precipitates when combined with soluble phosphates, carbonates and sulfates.

Surfactants that are suitable for use in the process of this invention are compounds or compositions that are capable of forming aqueous emulsions in the presence of hydrophilic and hydrophobic substances (solids or liquids). Preferably, the surfactants are water or water-alcohol soluble compounds or compositions. Examples of useful surfactants include, but are not limited to lecithin, monoglycerides, tartaric esters of monoglycerides, phosphated monoglycerides (e.g., as the monosodium salt), lactylated monoglycerides, acetylated monoglycerides, succinylated monoglycerides, ethoxylated monoglycerides, sorbitan esters, polysorbates, polyglycerol esters, sucrose esters, sodium stearoyl lactylate, propylene glycol esters and the like.

If needed only minor amounts of the enzymes are necessary to effect the desired further clarification. As will be readily recognized by those skilled in the art, these enzymes are commercially available in a variety of forms possessing varying levels of enzymatic activity. Accordingly, the concentration of the enzyme used may vary between the differing forms of the enzymes, between batches and between sources. It is considered within the ordinary skill of one in the art to determine the lysozyme and/or protease enzyme concentration required for further degrading of proteins and DNA holding together polysaccharide aggregates. Generally, the aqueous polymer solution is treated with about 10 ppm to about 1000 ppm (parts per million of aqueous xanthan solution) lysozyme and/or about 0.3 ppm to 2000 ppm protease enzyme. Preferably, the aqueous xanthan gum solution is treated with about 10 ppm to about 100 ppm lysozyme and/or about 0.3 ppm to about 500 ppm protease enzyme.

Accordingly, the process of this invention for the preparation of a clarified polysaccharide viscous solution comprising the steps of:

1) treating a fermentation broth containing a polysaccharide polymer with at least one sulfate and phosphate precipitation agent, from the group metal cat ions that are capable of forming insoluble precipitates with the residual sulfate and phosphate ion in the fermentation broth;

2) allowing the insoluble material to form on the surface of the cells and cell debris remaining in the polymer broth;

3) separating the precipitated metal sulfates and phosphates and cell debris by settling or centrifuging; and 4) treating the supernatant solution if needed with a lysozyme, a protease or a DNA degrading enzyme at a temperature of about 37.degree. C. to about 80.degree. C. at a pH of about 6 to about 9.

Alternatively, the clarification process may be conducted as a single operation wherein step 1 and step 2 and step 4 of the above processes are conducted simultaneously such that the polysaccharide polymer solution is simultaneously treated with at least one precipitating agent, and a protease enzyme or a lysozyme and a DNA degrading enzyme. In these embodiments, the process for the preparation of a clarified xanthan gum solution comprises treating a xanthan gum with at least one precipitating agent, and a protease enzyme or a lysozyme and a DNA degrading enzyme at a pH of about 6 to about 9 at a temperature of about 40.degree. C. to about 80.degree. C.

Alternatively, the clarification process may be conducted as an operation wherein step 4 is conducted before step 1 and step 2 and 3 of the above processes are conducted to digest and degrade more of the cells and cell debris to increase the binding of the precipitating agent by the addition of a protease enzyme or a lysozyme and a DNA degrading enzyme. In these embodiments, the process for the preparation of a clarified xanthan gum solution comprises treating a xanthan gum with at least one precipitating agent, and a protease enzyme or a lysozyme and a protease enzyme at a pH of about 6 to about 9 at a temperature of about 40.degree. C. to about 80.degree. C.

Advantageously, this process will produce a high purity polysaccharide soluble solution rather than solid that needs to be redissolved before use. The application of liquid polymer fluid provided by the process of this invention may also be useful in industrial application, for example, when xanthan gum is used to prepare a viscosifier to add to fluids used in oil well flooding operations. Other examples of such oil recovery fluids include payzone drilling fluids, workover fluids, completion fluids, and the like.

It is anticipated that the method of clarification of xanthan solutions disclosed herein, will also be suitable for the clarification of solutions of other fermentation-derived polysaccharides, for example, schizophyllan polymer, welan polymer, *sclerotium* polymer, alginate microbial polymer, gellan gum, and the like.

The theory of the process is complex; however, the implementation of the method is strait forward. It is believed that the high surface area of the cells and cell debris which also may contain adsorbed phosphates and sulfates will act as nucleation sites for the formation of insoluble crystals of metal phosphates, sulfates and carbonates and become attached or incorporated within the precipitates. Because most of the metal that for insoluble salts are also heavy metals such as barium, strontium, zinc and lead, The combined precipitated mass is much more dense that the cell and cell debris are alone. Therefore the rate of gravity separation is much faster through the viscous polymer solution.

The carbohydrates may be, for example, glucose, sucrose, fructose, lactose, galactose, soluble starch, corn starch, flours from various cereals, etc. Such carbohydrates are not necessarily used as highly refined materials; thus sugar-cane or sugar-beet molasses, or various residues of high sugar content may be used.

In addition to various carbohydrates as a carbon source the microorganisms also need other organic nutrients and vitamins. They also need inorganic nutrients such as phosphate, nitrogen, sulfur, carbonate and other trace elements. These are generally added in excess amounts to speed the rate of cell growth and polymer production. Not all of these media components are consumed at the end of fermentation. Because bio-polymer are generally recovered from fermentation broth by alcohol precipitation for either oil recovery or as a food additive, these residual media components are not recovered with the solid form of the polymer and therefore not a problem. Because the cells and cell debris would present a problem of bio-plugging if injected directly into the formation, prior methods of polymer recovery have become complex processes evolving multiple steps of enzyme additions and filtering to remove fermentation material to clarify the soluble polymer solution. These multiple step processes are expensive and often require complex processing facilities that are not practical to build at the oil field site. Therefore, most field application of bio-polymer for increasing the viscosity of waterflooding fluid use a powdered form of Xanthan or other biopolymers that is redissolved at the oil field site. The bio-polymers formed by fermentation in aqueous solution from these microorganisms are separated from the aqueous medium and treated to remove cell debris to be thereafter recovered in the solid state. They are dissolved again into water or brine to be used by injection into the wells, by admixing under stirring.

When biopolymers in the solid state are desired, the fermentation fluids are serially treated to separate said biopolymers from the aqueous medium according to known techniques, and preferably by solvent precipitation with alcohols such as methanol, ethanol or isopropanol, ketones such as acetone, etc., which solvents are thereafter recycled. The biopolymers are then separated by filtration or centrifugation and eventually subjected to further purification. If necessary, they are separated once more by filtration or centrifugation, and then dried according to various processes of producing a dry powder. Examples of available products of this type are Kelzan MF, Kelzan XCD and Xanflood from Kelco Co., Rhodopol 23 from Rhone Poulenc Co., Polytran CS 11 from CECA Co., etc.

The present disclosure relates to a water-soluble thickening composition, based on polysaccharides, which may be used, for example, in the operations of assisted oil recovery; this composition comprises (a) at least one crude fermentation fluid of a polysaccharide producing microorganism, which fluid has been clarified by co-precipitation of cells and cell debris along with insoluble metal sulfides, phosphates and carbonates. The denser precipitated material is then removed by high throughput centrifugation. The so-treated fermentation fluids may be further treated with enzymatic or chemical clarification treatments if needed. The soluble bio-polymer solution can then be mixed with biocides, surfactive agents and recycled production water for the direct injection into an oil reservoir formation as a viscosity increasing drive fluid. The surfactive agents are, for example: non-ionic, such as the condensation products of ethylene oxide with fatty alcohols or alkylphenols, anionic, such as the alkali metal sulfonates, for example, the alkylsulfonates, the arylsulfonates or the alkylarylsulfonates, the di-alkyl sulfates or the mixed alkyl and alkanolamine or alkali metal sulfates. Also the surfactive agents may be bio-surfactants made by fermentation.

The biopolymer solution is made resistant to possible bacterial decay by adding bactericides such as sodium azide, formaldehyde, alkali metal salts of chlorophenols, such as those sold by Rhone Poulenc Co. under the trade mark Cryptogil, mercury salts such as, for example, the ethylmercury thiosalicylates, the phenylmercury salts (for example acetate, borate or nitrate), chlorhexidine, 1,2-benzisothiazolone sold by Imperial Chemical Industries Co. under the trade mark Proxel AB Pate, a mixture of 5-chloro-2-methyl- 4-isothiazolin-3-one and 2-methyl-4-isothiazolin-3-one sold by Rohm and Haas Co. under the trade mark Kathon, etc. According to a preferred embodiment, the fermentation fluid is made free of cells and stabilized by addition of sodium azide (NaN.sub.3) which is used in an amount of, for example, 10 to 20,000 parts per million by weight (ppm), preferably 100 to 1,000 ppm. According to another preferred embodiment, Kathon is used in an amount of 10 to 1,000 ppm.

The biopolymer solution may be stored in containers and transported to the vicinity of the injection well by any adapted means, road, rail, ship, pipe, etc. If permitted by the plant in the vicinity of the oil field, the biopolymer solution may be manufactured on the field in sterile formation vessels of continuous or discontinuous type, as known in the art.

The biopolymer solution may be brought to the desired concentration or viscosity by dilution with formation water or injection brine. The useful concentrations of the biopolymer are usually between 0.005 and about 1.0 percent by weight and commonly between 0.05 and about 0.25% b.w. Such concentrations impart to the injection water containing various amounts of dissolved salts a viscosity of at least 2 centipoises at the reservoir temperature, but viscosities of about 100 centipoises or more may usefully be utilized in some cases. Such viscosities are usually sufficient to ensure an effective mobility reduction of the injection water and thus ensure better displacement of oil from the formation. If necessary, the pH of the biopolymer solution may be adjusted to the balanced pH of the formation and the oxygen content thereof may be controlled.

The biopolymer solution thus treated may then be pumped into the oil formation through one or more injection wells in conventional manner.

From an economic point of view it is advantageous to directly use a fermentation fluid of soluble bio-polymer after clarification by a simple one step addition and high throughput centrifugation if the crude soluble bio-polymer did not clogging of the formation rock when used for water flooding. The extent to which clarification must be done will depend on permeability of the formation rock. Some highly permeable rock formation may require only the one step precipitation and high throughput centrifugation.

Further details of the invention are illustrated by the following non-limiting examples.

Example 1: Materials and Methods

Flow Test

To make clogging apparent in the formation conditions, a so-called flow test is carried out; it comprises the following operations:

(a) The biopolymer solution prepared in standard conditions is first clarified by filtration under a constant pressure of 1 kg/cm$^2$ through 3 successive Millipore filters (distributed by Millipore Filter Corporation, Bedford, Mass., U.S.A.) of 3 micron pore size and 142 mm diameter, then through a Millipore filter of 0.45 micron pore size and 142 mm diameter. The resulting biopolymer solution is free of practically all bacterial residues and thus perfectly limpid.

(b) A pump is then operated to inject this clarified solution at constant flow rate through a Millipore filter of pore diameter higher than 0.45 micron. This injection is preferably carried out at constant pressure. The time to filter the first volume (10% of total) is measured. The time to filter the last 10% is used to calculate a filter ratio. The last 10% is slower if the is a filterability problem. A ratio of 1.0 would be an ideal polymer solution with not filterability problem. A more detailed review of this test is provided by Levitt and Pope in SEP 113845 2008.

Linear Coreflood Test with Berea Sandstone:

A more detailed testing procedure is to measure the performance of the polymer in an actual sample of Berea sandstone. This provides more detailed analysis of the polymer injectivity into a sandstone rock reservoir. The examples 1, 2 and 3 are of three differently clarified xanthan gum bio-polymer samples.

Example 2: GFF BP4 and BP5 Preparation

A single colony of *Xanthomonas campestris* (DSM19000, ATCC 13951, NRRL B-1459) growing overnight on a LB plate was inoculated in a growth broth (MY), and incubated at 28 C for 16 hours at 250 rpm (Rotations Per Minute) to generate a seed culture. The MY Broth comprises following chemical components.

| | | |
|---|---|---|
| Glucose | 20 | g/L |
| Peptone | 5 | g/L |
| Yeast extract | 5 | g/L |
| Malt extract | 5 | g/L |

To scale up the cell culture to 1 liter in a glass flask at laboratory, the seed culture was diluted 20-40 times in 1000 mL production medium (PM) containing following composition:

| | | |
|---|---|---|
| Glucose | 20 | g/L |
| KH2PO4 | 5 | g/L |
| MgSO4•7H2O | 0.2 | g/L |
| (NH4)2SO4 | 2.0 | g/L |
| Citric Acid | 2.0 | g/L |
| H3BO3 | 0.006 | g/L |
| ZnO | 0.004 | g/L |
| FeCl3•6H2O | 0.0024 | g/L |
| CaCO3 | 0.02 | g/L |
| NaOH | 2.2 | g/L |

The culture process, or fermentation, was carried out at 28 C for 72 hours with sufficient aeration to supply oxygen for optimal cell growth and xanthan gum production, resulted in a very viscous culture broth, a mixture consisting of microbial *Xanthomonas campestris* cell mass and its polymer product Xanthan gum.

To prevent cell growth and other microbial contamination in the cell culture broth, a biocide was added to the broth and mixed thoroughly in an incubator rotating at 250 rpm for 5-10 minutes. For instance, the biocide sodium azide (NaN3) was added to the broth to final concentration of 0.02-0.04% and then the broth could be kept at 4 C for up to 1-6 months.

Fresh *Xanthomonas campestris* cell culture broth and the broth kept at 4° C. for 1-6 months were used for generating Geo Fossil Fuels, LLC biopolymer product, referred to here as GFF BP4 and GFF BP5, according to the following procedure:

GFF BP4 Preparation

To remove cells and cell debris the fermentation broth was treated with previously reported methods to increase the filterability of xanthan gum. A 200 mL aliquot of *Xanthomonas campestris* cell culture broth kept at 4° C. for 1 month was transfer to a 500 mL Nalgene® Filter Storage Bottle and incubated in water bath at 55° C. for 1 hour.

Then 1 mL of 20% SDS was added to the 200 mL broth, the final concentration of SDS was 0.1%. The broth and SDS was mixed completely by inverting the bottle a number of times, and the bottle containing cell broth-0.1% SDS was further incubated at 55° C. for 1 hour. The broth-0.1% SDS solution turned to very sticky due to the DNA released from the cells, and DNA "strings" could be easily observed from pipette tip when the pipette tip was used to transfer 50 uL of the solution.

Next, 200 mL sterile and deionized water was added to the 200 mL cell broth with 0.1% SDS to make a 400 mL diluted cell broth with now a 0.05% SDS solution. It was then mixed completely by inverting the bottle a number of times.

The following chemical solutions was further added to the 400 mL diluted cell broth 0.05% SDS solution, one chemical was added and mixed completely before adding the next chemical.

| | |
|---|---|
| 1M Tris-HCl, pH 8.0 | 10 mL |
| 1M MgCl2 | 2 mL |
| DNase I (10 mg/mL) | 1 mL |

The mixed broth solution was incubated at 37° C. for 1 hour to let DNase I to completely digest the DNA released from the cells.

After the DNA digestion, Neutrase®, a protease, purchased from Sigma, was added in the amount of 0.3 ml of Neutrase® (0.8 U/g) along with 1.0 ml of 2.5 nM ZnSO4 solution to DNase I treated cell broth (total 400 mL). This treatment is believed to remove proteins and peptides released from the cells as well as the DNase I used to remove the DNA.

The digestion of proteins was carried out at 50° C. water bath for 2 hours after adding and mixing thoroughly the mixture of ZnSO4 and protease with the broth.

The DNase and protease treated cell broth was aliquoted to 50 mL Beckman® centrifuge tubes, and centrifuged at 20 C in Sorval superspeed using Sorval ss-34 rotor at 17000 rpm (RCF 27000 g) for 20 minutes.

The supernatant was saved and filtered through 0.45 micron polyether sulfone (PES) filter (Nalgene® Rapid-Flow™ Filter Units, VWR Cat #: 16211-068). This was to prepare the polymer solution for injection into a sandstone core to determine if this method of clarifying a fermentation broth directly without alcohol precipitation of the polymer was sufficient to allow for injection of this polymer directly into a reservoir formation. The filtrate was 57 cp in viscosity and was sent to a petroleum testing laboratory (Surtek Inc.) in Golden Colo. for coreflood testing.

Coreflood Testing Procedure

1. Berea sandstone cores were 2.54 cm in diameter and 12.5 cm in length.
2. Cores were saturated with production water reported for one known oil field the Chauvin Field in Lloydminster, Alberta to simulate a typical solution that might be encountered with polymer flooding.
3. The injected production water was used to determine the rock sample permeability to water, which was determined to be approximately 500 mD.
4. The injected fluid frontal advance rate was approximately 1 foot per day.
5. Prior to injection of the xanthan polymer prepared directly from the fermentation broth, the polymer solution was mixed with the production water.
6. The mixing of the GFF BP4 sample with the simulated production water developed a precipitate, which was filtered out requiring seven changes of Whatman GF/D 2.7 micron glass micro filters. This process was time consuming and removed 0.43 grams of precipitated material form 100 ml of solution.
7. The viscosity of the unfiltered mixture was 42.3 cp which dropped to 32.2 after this filtration.
8. After filtration the polymer solution was used to complete the coreflood experiment.
9. A control coreflood was preformed with the same procedure using a commercial dry powder form of xanthan gum (Kelzan XCD) intended for oil recovery.
10. The control sample of polymer, Kelzan XCD, was directly dissolved in the production water by mixing at 800 RPM in a Waring blender. Because Kelzan XCD is a dry powder the high shear is needed to hydrate the polymer. There was no precipitate with the hydrated Kelzan sample.

Results of the Coreflood Injectivity Test

Both bio-polymer solutions showed injectivity problems. The injectivity problems were believed to be due to insoluble material filtered by the sandstone surface. The Kelzan XCD bio-polymer and the GFF BP4 flowed through the core after entering the core surface. The injection of polymer continued until approximately 8 pore volumes of each polymer solution was pumped into the cores. The concentrations eluted from each core were determined by viscosity measurements for each pore volume exiting the test sandstone core. After approximately 8 pore volumes of bio-polymer solution, the input fluid was changed back to brine. At least 4 pore volumes of simulated produced water were injected to flush out the polymer solution from the core. Differential pressures were measured from the injection face to 1 inch from the injection face, from 1 inch to 3 inches from the injection face, from 3 inches from the rear of the core and from the injection face to the end of the core. This data was used to determine the change in resistance factors of the Berea sandstone as a result of the polymer flooding. Analysis of this data indicated that front end resistance factors and plugging of both cores by both test bio-polymer solutions had had occurred. The front end resistance factors continually increased as the polymer solution was injected. After the test, an inspection of the sandstone face showed that material was filtered from the polymer solution. The residual resistances, after flushing with 4 pore volumes of water, were higher than the initial resistance factor for both samples indicating that material is not being flushed out. The residual resistance factor was higher for the GFF BP4 than the Kelzan XCD sample. This was indicted by ratio of the pressure for the total length after 4 pore volumes of water flushing to before polymer injection being about 200 for the Kelzan and about 250 for the GFF BP4 samples. Therefore, the clarification procedure used on the polymer produced directly from fermentation broth did not perform as well as commercially prepared and clarified xanthan gum with regards to the face-plugging.

Once both GFF BP4 and Kelzan XCD entered the core, the resistance factors indicated that both bio-polymer solutions flowed through the core. Analysis of the effluent polymer concentration and viscosity indicated that there was some retention of bio-polymer by the Berea sandstone core. The original viscosity of the Kelzan XCD sample was 41.5 cP. The original injected viscosity of the GFF BP4 sample was 32.2 which was lower due to the extensive filtering that was needed as a result of the unexpected precipitation when diluted into the simulated production water. The calculated asymptote viscosity of the effluent polymer solution was 33.2 for the Kelzan XCD xanthan polymer or 80% of the initial viscosity. The calculated asymptote viscosity was 28.2 or 87% of the initial viscosity. Therefore the retention of the polymer clarified directly from the broth without alcohol precipitation was less retained by the Berea sandstone than the rehydrated bio-polymer produced by alcohol precipitation from the fermentation broth.

However, the method of clarification of bio-polymer from fermentation broth by means of enzyme treatment and centrifugation and filtration were unable to produce a clarified fluid that was suitable for injection into a oil containing formation because soluble contaminates remaining from the fermentation broth were interacting with the formation water and causing precipitates that were face plugging the sandstone. If the sample had been injected directly into core or injection well bore a precipitate would have formed and would have caused severe plugging.

Analysis of the simulated water recipe and the fermentation media recipe suggested that there were possible combination that could lead to a precipitated to form when the two were mixed together. When the two solutions, free of any bacteria or polymer, were mixed together there was a precipitate that did occur. The assumption was that metal ions found in this formation and that might be found in many oil reservoirs could form insoluble precipitates with the residual sulfate, phosphate and carbonate needed for the growth of bacteria and production of bio-polymers. These residual media components would generally not be a problem with xanthan gum clarified by prior art methods because these soluble materials would stay in solution during the alcohol precipitation step and centrifugation step used to make the dry powder form of xanthan.

The media soluble components could be removed from the polymer by ion exchange or dialysis or high molecular weight membrane separation or other known methods of removing low molecular weight ions for a polymer solution. However, it was discovered that a co-precipitation process could remove both the cell debris and the residual media chemicals by addition of soluble heavy metal salts that could form insoluble precipitated sulfates, phosphates or carbonates. This could be done together as part of the clarification process. In fact, the increased density and the nucleation of insoluble metal sulfides and phosphates and carbonates crystals on the cell surfaces made the removal by centrifugation more efficient.

A new clarification method was devised wherein the ions found in reservoir water were mixed with the fermentation broth along with the surfactant and enzymes to digest the cell debris and before centrifugation or filtering. It was discover that combined step made the clarification of the bio-polymer simpler, faster and more effective. This new process was then used on a fermentation broth prepared the same way as for sample GFF BP4.

Example 3: GFF BP5 Preparation 550 mL pool of 3 *Xanthomonas Campestris* cell culture broth kept at 4 C for 1, 3 and 4.5 month was transfer to a 1000 mL Nalgene Filter Storage Bottle. Then 2.75 mL of 20% SDS was added to the 550 mL cell broth, the final concentration of SDS was 0.1%. The broth and SDS was mixed completely by inverting the bottle a number of times, and the bottle containing cell broth-0.1% SDS was further incubated at 55 C for 2 hours. The broth-0.1% SDS solution turned to very sticky due to the DNA released from the cells, and kept on lab bench for 16 hours (overnight). A simulated reservation produced water, Chauvin Produced Water, containing 100,000 ppm (10%) TDS (total dissolved salt: 100.12 g/L) comprising components listed below, was freshly prepared:

| NaCl | 77 | g/L |
| --- | --- | --- |
| MgCl2•6H2O | 12 | g/L |
| CaCl2•2H2O | 8.1 | g/L |
| KCl | 1.03 | g/L |
| FeCl3 | 0.02 | g/L |
| BaCl2•2H2O | 0.3 | g/L |
| SrCl2•6H2O | 0.3 | g/L |
| NaHCO3 | 1.37 | g/L |

Two aliquots of 100 mL cell broth-0.1% SDS mixture described above was transferred to two 500 mL storage bottles labeled as A and B, then 100 mL Chauvin Produced Water was added to each bottle and mixed thoroughly by inverting the bottles for a number of times.

The following chemical solutions were further added to both bottle A and bottle B, containing cell broth-0.1% SDS-Chauvin Produced Water mixture. One chemical was added each time and mixed completely before next chemical was added.

| 1M Tris-HCl, pH 8.0 | 5.0 mL |
| --- | --- |
| DNase I (10 mg/mL) | 0.5 mL |

The mixed broth solution was incubated at 37 C for 1.5 hour to let the enzyme completely digest the DNA released from the SDS treated cells.

Bottle A was used as a control, with no added Neutrase® to digest proteins in solution. It was incubated at 37 C for additional 1 hour.

The Neutrase® and ZnCl2 were added to bottle B (200 mL in total) accordingly:

| 1000X (2.5 mM) ZnCl2 | 0.2 mL |
| --- | --- |
| Neutrase (0.8 U/g) | 0.1 mL |

Then, the digestion of proteins was carried out at 50° C. water bath for 1 hour upon the adding and mixing thoroughly of ZnCl2 and Neutrase® with the broth.

The DNase and Neutrase® treated cell broth in bottle A and DNase only control Bottle B, ware aliquoted to 500 mL Beckman centrifuge tubes, and centrifuged at 20° C. in Beckman Aventi using rotor JA-17 rotor at 12000 g) for 20 minutes.

The supernatants were saved and further filtered through a Whatman GF/D 2.7 micron glass filter paper. For each sample, the protease treated and the untreated control, only one filter paper was used to filter through the cell broth viscous solution, the filtrate was stored at 4° C.

To see if there was additional precipitates formed in the sample solution, when sample A and sample B was stored at 4 C for two weeks, centrifugation was carried out for both samples in Beckman Aventi using rotor JA-17 rotor at 12000 g for 25 minutes at 20 C. Obvious precipitate was observed in both samples and was discarded, and the supernatant was saved, easily filtered through one Whatman GF/D 2.7 micron glass filter paper, and filtrate was stored at 4 C.

To see if there was additional precipitates formed in the sample solution at a higher centrifuge force, after sample A and sample B solution was stored at 4 C for another two weeks, and was aliquoted to 50 mL Beckman centrifuge tubes, and centrifuged at 20 C in Sorval superspeed using Sorval ss-34 rotor at 18000 rpm (RCF 30000 g) for 22 minutes, yellowish precipitates were observed and discarded, the supernatant was much more clear after this centrifugation.

To see if there was even more precipitates at a much higher centrifuge force, centrifugation was carried out for both samples in Sorval superspeed using Sorval ss-34 rotor at 20000 rpm (RCF 37000 g) for 20 minutes at 20 C.

Little precipitates (almost no precipitate, or precipitate hardly seen) were observed. The supernatant from each centrifuge tube was very clear and pooled as GFF biopolymer product, GFF BP5 (52CP in viscosity), sent to Surtek for a new linear coreflood experiment.

Example 4: Third Linear Core Flood Experiment

A third linear core flood was preformed with GFF BP5 to determine if the addition of a new co-precipitation step could solve the incompatibility problems with the clarified bio-polymer made directly from the fermentation broth. Also this third test was to determine if the modified procedure could produce a polymer solution that had less retention by the sandstone rock than the commercial alcohol precipitated xanthan gum polymer commonly used for oil recovery.

The third test was done in a similar procedure as the first two corefloods. The polymer was stable when mixed with the ion and salt containing production water. The GFF BP5 sample still showed some injectivity issues but not as severe as either GFF BP4 or Kelzan XCD. The GFF BP5 sample retention was similar to GFF BP4 with the produced fluid reaching an asymptotic value of 90% of the injected solution viscosity. After the polymer solution the core was flooded with the brine as before. In this case the resistance factor for GFF BP5 declined to a lower value with injection of the simulated Chauvin production water than either Kelzan XCD or GFF BP4 experiments. The total resistance factor ratio of after the 4 pore volume brine flush was about 25 for GFF BP5 as compared to a ratio of 200 for the Kelzan XCD bio-polymer and a ratio of 250 for the GFF BP4 bio-polymer.

Conclusions:

Direct injection of a fermentation broth of a cell free polysaccharide producing microorganism into an oil reservoir is not expected to work due to components that will cause face-plugging of the formation rock. The face-plugging components are cells, cell aggregates, cell debris, and media nutrient salts that can interact with the reservoir water that can form insoluble precipitates.

1) The addition of soluble salts of heavy metals that form insoluble sulfides, phosphates and carbonates can be used to rapidly and inexpensively remove these ions form solution thereby preventing the formation of insoluble precipitates within the formation when the formation water is encountered.

2) These metal salts can, for example, be from the reservoir's production water or concentrates of the production water or made up of chemical salts that are known to form insoluble sulfates, phosphates and carbonates. Some non-limiting examples are: barium, lead, strontium, zinc, calcium, magnesium, iron, mercury and silver.

3) The precipitation of the media material can be combined with the cell material clarification process and facilitates centrifugation removal of the cell aggregates and cell debris by increasing the density of the cell material when the insoluble crystals form at the cell surface. The higher density of the combined cell mass and heavy metal sulfates and phosphates are easier to remove from the viscous polymer solution by centrifugation than by filtering or by centrifuging the lighter cell mass material alone.

4) The combined metal sulfate and phosphate precipitate and enzyme clarification process with centrifugation removes the impurities from the aqueous solution, leaving the bio-polymer in solution. It is a simpler and lower cost process than the current commercial process for producing oil grade xanthan gum or other polysaccharide polymer wherein the soluble polymer is made insoluble by addition of organic solvents.

5) It is possible to produce a bio-polymer that is equal or better for injection into oil reservoirs than polymer powders produced by alcohol precipitation of the polymer.

Example 5: Cells, Cell Debris and Sulfate were Removed by Barium Chloride

Viscous broth of *Xanthomonas campestris* 20170522D was generated in a 2-liter fermenter at 28° C. for 84 hours, using PM79 medium containing 5% glucose as the only carbon source. The viscosity of the broth was measured as 9296 centipoles (cp) by Brookfield DV2T Viscometer at 25° C.

To make it easy to work, the broth 20170522D was diluted 5× in MQ water. Briefly, the broth was incubated at 55° C. for 60 minutes, followed by adding 5×MQ water in weight and mixing it at 250 rpm for 10 minutes at room temperature.

The 5× diluted broth 20170522D was aliquoted 5 grams to each conical tube, and each divalent salt of $CaCl_2.2H2O$, $MgCl_2.6H2O$, $BaCl_2.2H2O$ and $SrCl_2.6H2O$ was added to an individual tube to final concentration 40 mM, and no divalent salt was added to the control tube. To mix the chemical and the broth thoroughly, and to make sure the chemical reactions were fully completed, all the tubes including the control tubes were incubated at 250 rpm for 30 minutes at room temperature.

The samples in conical tubes were centrifuged at 21,000 g RCF (relative centrifugal force) for 20 minutes at room temperature. The supernatant was saved and stored at room temperature for downstream sulfate and phosphate tests.

The precipitate was washed 2 times with PBS (phosphate buffered saline), and resuspended in 200 μL PBS per sample, the pellet should contain biomass (cells and cell debris) and other insoluble parts (salt etc.). The control (C) was centrifuged as those treated with individual divalent, the total protein in control pellet should reveal the total protein in the cells by centrifuging the 5× diluted broth.

The quantity of total proteins in precipitate of divalent treated samples should be an indication of total cells co-precipitated with the insoluble divalent salts, for example, cells may be pulled down by insoluble $BaSO4$.

Quantification of total protein in the pellets was carried out in 96-Well Plates, using Pierce BCA Protein Assay Kit. Standard samples of BSA (bovine serum albumin) with concentration (μg/mL) of 0, 5, 12.5, 25, 125, 250, 500, 750, 1000, 1500, 2000 were prepared in PBS, and the microplate quantification procedure was carried out followed the manufacturer's instructions:

1. Pipette 25 μL of each standard or unknown sample replicate into a microplate well
2. Add 200 μL of the WR (working reagent) to each well and mix plate thoroughly on a plate shaker for 30 seconds.
3. Cover plate and incubate at 37° C. for 30 minutes.

4. Cool plate to room temperature. Measure the absorbance at 562 nm on plate reader Spectra Max Plus.

BCA protein assay results (see below) showed that total protein in the control (C) was 271 μg/mL, and that in treatment with 40 mM BaCl2 was 626 μg/mL. There was 2.3 times total protein in pellets of 40 mM BaCl2 treatment than that in the control, suggesting 40 mM $BaCl_2$ was able to precipitated two times or more cells than that in the control. The results also revealed that $SrCl_2$ co-precipitated 11% more cells than that in the control, however, $CaCl_2$ and $MgCl_2$ had almost co-precipitated no more cells than the control.

| Sample | Wells | Values | Outliers | Result | MeanResult | Std. Dev. | CV % |
|---|---|---|---|---|---|---|---|
| 1. 0522D_no divalent (C) | G3 | 0.34 | | 268.674 | 271.322 | 3.745 | 1.4 |
| | G4 | 0.346 | | 273.971 | | | |
| 2. 0522D_40 mM CaCl2 | F3 | 0.347 | | 275.6 | 271.017 | 6.482 | 2.4 |
| | F4 | 0.338 | | 266.434 | | | |
| 3. 0522D_40 mM MgCl2 | E3 | 0.35 | | 278.452 | 278.248 | 0.288 | 0.1 |
| | E4 | 0.35 | | 278.044 | | | |
| 4. 0522D_40 mM BaCl2 | D3 | 0.716 | | 651.317 | 625.804 | 36.081 | 5.8 |
| | D4 | 0.666 | | 600.291 | | | |
| 5. 0522D_40 mM SrCl2 | C3 | 0.368 | | 296.886 | 301.775 | 6.914 | 2.3 |

An independent experiment showed that total protein in the control (C) was 111 μg/mL, and that in treatment with 40 mM BaCl2 was 230 μg/mL when samples in conical tubes were centrifuged at 16,000 RCF (relative centrifugal force) for 20 minutes at room temperature. These results suggested that less than half the cells was pulled down 16,000 RCF comparing to that pull down by 21,000 RCF.

| Sample | Wells | Values | Outliers | Result | MeanResult | Std. Dev. | CV % |
|---|---|---|---|---|---|---|---|
| 0522D_no divalent (C) | H3 | 0.185 | | 117.082 | 111.511 | 7.878 | 7.1 |
| | H4 | 0.17 | | 105.941 | | | |
| 0522D_40 mM CaCl2 | G3 | 0.142 | | 85.743 | 87.396 | 2.338 | 2.7 |
| | G4 | 0.146 | | 89.049 | | | |
| 0522D_40 mM MgCl2 | F3 | 0.136 | | 81.574 | 79.166 | 3.405 | 4.3 |
| | F4 | 0.129 | | 76.758 | | | |
| 0522D_40 mM BaCl2 | E3 | 0.341 | | 228.994 | 230.144 | 1.626 | 0.7 |
| | E4 | 0.344 | | 231.294 | | | |
| 0522D_40 mM SrCl2 | D3 | 0.13 | | 77.477 | 78.483 | 1.423 | 1.8 |

Sulfate quantity was determined by a number of sulfate test strips with 0-1600 mg/mL (ppm) detection level, and results obtained for samples from a number of independent experiments were almost identical. Briefly, water Quality Test Strips was the most sensitive one which can detect 0-500 ppm sulfate precisely, the test results showed sulfate in the 40 mM BaCl2 treated sample contained 0 ppm sulfate, suggesting sulfate was completely removed by BaCl2, or the sulfate was significantly removed after the treatment, therefore the sulfate content left in the sample was at very low level and was not detected.

| Sulfate Test Results Using Water Quality Test Strips | | |
|---|---|---|
| Sample | | Sulfate (mg/L) |
| 1. | 0522D_control | 500 |
| 2. | 0522D_40 mM CaCl2 | 250 |
| 3. | 0522D_40 mM MgCl2 | 500 |
| 4. | 0522D_40 mM BaCl2 | 0 |
| 5. | 0522D_40 mM SrCl2 | <250 |

Conclusions:

The results of the present example show that of the divalent metal ions tested, barium chloride is most effective at reducing both the sulfate concentration and total cell protein from the fermentation broth. This method can be used to reduce the amount of cells and cell debris by precipitation of sulfate and other anion contaminates in the fermentation broth that could cause problems when mixed with formation water. By reducing the amount of cell material from the broth the downstream polymer solution clarification should require less enzyme addition, centrifugation or filtration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A method for the production of an aqueous composition suitable for direct use in a water-flood oil recovery process, which comprises a clarified fermentation fluid containing at least one dissolved polysaccharide, comprising the consecutive steps of:
   (a) culturing a polysaccharide-producing microorganism in an aqueous culture medium to produce an aqueous culture containing said dissolved polysaccharide therein; and
   (b) clarifying the resultant aqueous culture from step (a), the clarification being effected by an addition of at least one soluble metal ion known to form insoluble precipitates with anions of sulfate, phosphate or carbonate in excess of the amount of said anions in the fermentation broth; and (c) incubating the metal ions with the fermentation broth to form a precipitate on the cells and cell debris; and (d) removing the precipitate by gravity settling and/or centrifugation, and recovering said resultant clarified fermentation fluid containing said dissolved polysaccharide, wherein said steps (a)-(d) follow each other in this order, without any intervening steps.

2. The method according to claim 1 consisting essentially of steps (a)-(d).

3. The method according to claim 1, wherein the clarification treatment is effected by centrifugation of at least 4,000 g.

4. The method according to claim 1, wherein the polysaccharide-producing microorganism is a microorganism of the *Xanthomonas* type.

5. The method according to claim 1, wherein the clarified fermentation fluid has a polysaccharide concentration of 0.005 to 1% by weight and a viscosity of from 5 to 500 centipoises at the reservoir temperature.

6. The method according to claim 1, wherein said precipitating agent is soluble salt of a metal ion known to form low solubility salts of sulfate, carbonate or phosphate.

7. The method according to claim 1, wherein said precipitating agent is barium ion.

8. The method according to claim 1, wherein said precipitating agent is strontium ion.

9. The method according to claim 1, wherein said precipitating agent is calcium ion.

10. The method according to claim 1, wherein said precipitating agent is zinc ion.

11. The method according to claim 1, wherein said precipitating agent is lead ion.

12. The method according to claim 1, wherein said precipitating agent is mercury ion.

13. The method according to claim 1, wherein said precipitating agent is magnesium ion.

14. The method according to claim 1, wherein the microorganism is selected from the group consisting of: the *Xanthomonas* genus, particularly the *Xanthomonas campestris*, *Xanthomonas begoniae*, *Xanthomonas pisi*, *Xanthomonas vesicatoriae*, *Xanthomonas carotae*, *Xanthomonas hederae*, *Xanthomonas incanae*, *Xanthomonas malvacearum*, *Xanthomonas phaseoli*, *Xanthomonas vasculorum*, *Xanthomonas vitians* and *Xanthomonas pelargonii* species; the *Arthrobacter* genus, particularly the *Arthrobacter stabilis* and *Arthrobacter* viscous species; the *Erwinia* genus, particularly the *Erwinia Tahitica* species; the *Azotobacter* genus, particularly the *Azotobacter indicus* species; and fungi of the *Sclerotium* genus, particularly the *Sclerotium glucanicum* and *Sclerotium rolfsii* species.

15. The method according to claim 14, wherein the microorganism is *Xanthomonas campestris*.

16. A clarified fermentation fluid obtained by a method according to claim 1.

17. The clarified fermentation fluid obtained by a method consisting essentially of steps (a)-(d) of the method according to claim 1.

18. An aqueous composition suitable for direct use in a water-flood oil recovery process, which comprises a clarified fermentation fluid containing at least one dissolved polysaccharide, said clarified fermentation fluid being obtained by a method according to claim 1.

19. The aqueous composition of claim 18, wherein said clarified fermentation fluid is obtained by a method consisting essentially of steps (a)-(d) of the method according to claim 1.

20. A method for the production of an aqueous composition suitable for direct use in a water-flood oil recovery process, which comprises a clarified fermentation fluid containing at least one dissolved polysaccharide, comprising the consecutive steps of:

(a) culturing a polysaccharide-producing fungal microorganism selected from the group consisting of the *Sclerotium* genus and the *Schizophyllium* genus, in an aqueous culture medium to produce an aqueous culture containing said dissolved polysaccharide therein; and (b) clarifying the resultant aqueous culture from step (a), the clarification being effected by an addition of at least one soluble metal ion known to form insoluble precipitates with anions of sulfate, phosphate or carbonate in excess of the amount of said anions in the fermentation broth; and (c) incubating the metal ions with the fermentation broth to form a precipitate on the cells and cell debris; and (d) removing the precipitate by gravity settling and/or centrifugation, and recovering said resultant clarified fermentation fluid containing said dissolved polysaccharide, wherein said steps (a)-(d) follow each other in this order, without any intervening steps.

21. The method of claim 20, wherein the polysaccharide-producing fungal microorganism is selected from the group consisting of *Sclerotium glucanicum* and *Sclerotium rolfsii*.

\* \* \* \* \*